United States Patent [19]

Eisfeld et al.

[11] 4,207,255

[45] Jun. 10, 1980

[54] MANUFACTURE OF VERY PURE HALONAPHTHALIC ACID ANHYDRIDES

[75] Inventors: Wolfgang Eisfeld; Walter Disteldorf; Albert Hettche, all of Ludwigshafen, Fed. Rep. of Germany

[73] Assignee: BASF Aktiengesellschaft, Fed. Rep. of Germany

[21] Appl. No.: 850,239

[22] Filed: Nov. 10, 1977

[30] Foreign Application Priority Data

Nov. 24, 1976 [DE] Fed. Rep. of Germany ....... 2653346

[51] Int. Cl.² ............................................. C07C 63/34
[52] U.S. Cl. ................................................. 260/546
[58] Field of Search ................................... 260/546 R

[56] References Cited

U.S. PATENT DOCUMENTS

| | | | |
|---|---|---|---|
| 3,646,069 | 2/1972 | Okada et al. | 260/345.2 |
| 4,097,492 | 6/1978 | Rohrscheid | 260/345.2 |

FOREIGN PATENT DOCUMENTS

| | | |
|---|---|---|
| 2343964 | 4/1975 | Fed. Rep. of Germany . |
| 48-1068 | 1/1973 | Japan . |
| 48-75555 | 10/1973 | Japan . |

*Primary Examiner*—Joseph E. Evans
*Attorney, Agent, or Firm*—Keil & Witherspoon

[57] ABSTRACT

Pure halonaphthalic acid anhydrides are prepared from haloacenaphthenes by oxidation with nitric acid in a mixture of aliphatic carboxylic acid, water and nitric acid in the presence of vanadate, with or without further metal salts, at an elevated temperature and the reaction product is isolated and subjected to an oxidative after-treatment with hypochlorite in aqueous solution at a pH of from 9 to 12 at an elevated temperature. The products are intermediates for the manufacture of optical brighteners.

5 Claims, No Drawings

MANUFACTURE OF VERY PURE HALONAPHTHALIC ACID ANHYDRIDES

The present invention relates to a process for the manufacture of pure halonaphthalic acid anhydrides from haloacenaphthenes by oxidation with nitric acid. The process is characterized in that the oxidation is carried out in a mixture of an aliphatic carboxylic acid, water and nitric acid in the presence of a vanadate, with or without one or more further metal salts, at an elevated temperature, and that the reaction product is isolated and subjected to an oxidative aftertreatment with a hypochlorite in aqueous solution at a pH of from 9 to 12 at an elevated temperature.

Haloacenaphthenes are acenaphthenes substituted by fluorine, bromine or preferably, chlorine, especially in positions 3, 5 and/or 6.

Suitable aliphatic carboxylic acid solvents for the oxidation with nitric acid are, in particular, acetic acid, propionic acid, n- and i-butyric acid and pentanecarboxylic acids. Because of their insufficient stability to oxidation under the reaction conditions, formic acid and long-chain fatty acids are less suitable. Of course it is also possible to use substituted fatty acids, eg. haloacetic or halopropionic acids.

The system of fatty acid, nitric acid and water should, for reasons of safety, in order to avoid the formation of an acyl nitrate, always contain some water. Amounts of 1% by weight appear adequate. An upper limit is imposed on the water content by the decreasing solvent power and decreasing reactivity of the system. If the reaction is carried out at temperature up to the boiling point of the mixture, the water content should advantageously not exceed 20% by weight; if the reaction is carried out under pressure at up to 160° C., the water content should advantageously not exceed 30% by weight. Preferably, the reaction is carried out under atmospheric pressure, with water contents of from 1 to 15% by weight. As a rule, the oxidation is carried out at from 70° to 160° C., and preferably at from 90° to 110° C.

The nitric acid content of the oxidation system is usually kept within the limits of from 0.01 to 30% by weight, preferably from 0.01 to 20% by weight. The oxidation is advantageously carried out by adding nitric acid to a mixture of fatty acid, haloacenaphthene, water and catalyst at a rate such that the heat of reaction can be removed efficiently. As a rule, the reaction starts at nitric acid concentrations of from 0.05 to 2% by weight, depending on the temperature used and on the water content of the system. The nitric acid added may be dilute or concentrated; it is particularly desirable that the water content in the oxidation system should not exceed the above maximum of 30% by weight, in which amount the water of reaction formed during the oxidation must be included. Nitric oxides ($N_2O_3$ and $N_2O_4$) can also be used in place of nitric acid. To complete the oxidation it is advantageous, when the main reaction has subsided, either to increase the nitric acid concentration whilst keeping the temperature unchanged or to raise the temperature, if necessary under superatmospheric pressure, whilst keeping the nitric acid concentration the same. The pressure applied must at least equal the vapor pressure of the system and should, for safety reasons, be less than three times the vapor pressure of water, at the temperature employed.

The use of pentavalent vanadium, for example in the form of ammonium vanadate or sodium vanadate, generally in a concentration of from about 0.1 to 5%, preferably from 0.5 to 2%, by weight based on haloacenaphthene (corresponding to from about 0.01 to 0.5%, preferably from 0.05 to 0.2%, by weight based on the fatty acid/water/nitric acid system) is necessary to achieve a good yield. The addition of a manganese salt and/or a copper salt to the vanadate has proved particularly advantageous since it improves both the yield and the quality of the end product. The manganese or copper salt can replace up to 75% of the vanadate. The addition of iron, cobalt or nickel salts also improves the quality of the end product over that obtained when using vanadate alone.

It is true that the crude product which can be isolated by crystallization after the nitric acid oxidation consists predominantly of the desired halonaphthalic acid anhydride, but it still contains intermediates and by-products, which cannot be removed to a sufficient degree by conventional redissolving in alkali and reprecipitation, with or without an oxidative or reductive aftertreatment, for example with $H_2O_2$, hypochlorite, sulfite or dithionite.

Surprisingly, halonaphthalic acid anhydrides of sufficient purity for all requirements are obtainable by dissolving the isolated crude product, suitably in the form of its alkali metal salt, in water at a pH strictly maintained at from 9 to 12, and subjecting the resulting solution to an oxidative after-treatment with a hypochlorite, particularly an alkali metal hypochlorite, in the said pH range at an elevated temperature, particularly from 60° to 100° C. After removing undissolved by-products, for example by filtration, acidifying the solution gives a colorless halonaphthalic acid anhydride with the elementary analysis and color numbers to be expected of a very pure product. The pH range of from 9 to 12 is advantageously maintained by carrying out the treatment in an aqueous alkali metal carbonate solution or in a solution buffered with carbonate. It is important that there should be no deviation from the stated pH range even for brief periods or locally.

Further details are given in the Examples and Comparative Examples which follow, in which parts and percentages are by weight, unless stated otherwise. The purity criteria reported are the chlorine content, the residual nitrogen content and the iodine color number in alkaline solution:

EXAMPLES 1 to 11 and COMPARATIVE EXAMPLES 12–14

(a) Oxidation with $HNO_3$: 100 parts of 5,6-dichloroacenaphthene of 85% purity in 830 parts of carboxylic acid (see Table 1) and 10 parts of water are heated with 1 part of catalyst (see Table 1) at 100° C. whilst stirring; the material dissolves almost completely. 480 parts of 65% strength $HNO_3$ are added uniformly over a period of 6 hours whilst maintaining the temperature at from 100° to 105° C. The nitrous fumes which constitute the off-gas escape through a reflux condenser. To complete the oxidation, the mixture is stirred for 6 hours under reflux (105°–108° C.). It is then cooled to room temperature and the solid, part of which has already precipitated during the reaction, is collected and washed neutral with water. Dried samples of the crude product give the following typical analytical values: chlorine 25.3–25.8% (theory 26.6%), nitrogen 0.9–1.1% (theory 0%), iodine color number >100 (5% strength solution in 0.5 N KOH).

(b) Purification: The moist crude product is heated with 1,570 parts of water and 72 parts of potassium carbonate at 90° C. 39 parts of 50% strength potassium hydroxide solution and 80 parts of aqueous sodium hypochlorite solution having an active chlorine content of from about 10 to 14% are added uniformly in the course of about 1 hour, with thorough stirring, at a rate such that the pH does not exceed 12.0 or fall below 9.0 at any time. After a further hour at 90° C., insoluble material is filtered off and the filtrate is cooled to 45°–50° C. and brought to pH 1 with sulfuric acid. The 4,5-dichloronaphthalic acid anhydride which has precipitated is collected, washed neutral with water and dried at 100° C. under reduced pressure.

Table 1 shows the yields and purities achieved in Examples 1 to 11, as a function of the carboxylic acid used as a solvent for the oxidation, and as a function of the oxidation catalyst employed. Comparative Examples 12–14 show that in the absence of a vanadate catalyst no useful dichloronaphthalic acid anhydride is obtained. Purification was carried out under identical conditions for all of Examples 1 to 14.

COMPARATIVE EXAMPLE 16

The oxidation with $HNO_3$ is carried out as described in Example 2 and the purification is carried out as described hereafter, at pH 13–14: the moist crude product is heated with 1,570 parts of water and 162 parts of 50% strength potassium hydroxide solution at 90° C., whereupon it dissolves slowly. 80 parts of aqueous sodium hypochlorite solution containing 10% of active chlorine are added uniformly in the course of 2 hours and stirring is then continued for 1 hour at 90° C. The further working up gives 77.3 parts of 4,5-dichloronaphthalic acid containing 26.4% of chlorine and 0.5% of residual nitrogen and having an iodine color number of 86. In this form, the product cannot be used for the manufacture of optical brighteners.

COMPARATIVE EXAMPLE 17

The oxidation and purification are carried out as described in Example 8, with the sole difference that 36 parts of perhydrol (30% strength hydrogen peroxide solution) are used instead of hypochlorite. 73.6 parts of 4,5-dichloronaphthalic acid anhydride containing 26.2% of chlorine and having an iodine color number of >100 are obtained.

TABLE 1
(for explanation, see text)

| Example No. | Carboxylic acid used for the oxidation | Catalyst composition and amount (parts) | 4,5-dichloronaphthalic acid anhydride after reprecipitation | | | |
|---|---|---|---|---|---|---|
| | | | Yield (parts) | Cl content (%)+ | N content (%) | Iodine color number (5% strength solution in 0.5N KOH) |
| 1 | acetic acid | 1.0 $NH_4VO_3$ | 73.2 | 26.7 | 0.05 | 35 |
| 2 | acetic acid | 0.5 $NH_4VO_3$ + 0.5 $Mn(NO_3)_2 \cdot 4 H_2O$ | 78.4 | 26.6 | 0.03 | 22 |
| 3 | acetic acid | 0.5 $NH_4VO_3$ + 0.5 $Cu(NO_3)_2 \cdot 3 H_2O$ | 74.8 | 26.7 | 0.04 | 31 |
| 4 | acetic acid | 0.65 $NH_4VO_3$ + 0.35 $Cu(NO_3)_2 \cdot 3 H_2O$ | 73.9 | 26.8 | 0.03 | 25 |
| 5 | acetic acid | 0.5 $NH_4VO_3$ + 0.5 $Fe(NO_3)_2 \cdot 9 H_2O$ | 70.4 | 26.3 | 0.04 | 26 |
| 6 | acetic acid | 0.5 $NH_4VO_3$ + 0.5 $Co(NO_3)_2 \cdot 6 H_2O$ | 72.3 | 26.4 | 0.04 | 25 |
| 7 | propionic acid | 1.0 $NH_4VO_3$ | 75.5 | 26.5 | 0.03 | 13 |
| 8 | propionic acid | 0.5 $NH_4VO_3$ + 0.5 $Mn(NO_3)_2 \cdot 4 H_2O$ | 82.2 | 26.5 | 0.01 | 7 |
| 9 | propionic acid | 0.5 $NH_4VO_3$ + 0.5 $Cu(NO_3)_2 \cdot 3 H_2O$ | 80.4 | 26.5 | 0.02 | 10 |
| 10 | butyric acid | 0.5 $NH_4VO_3$ + 0.5 $Mn(NO_3)_2 \cdot 4 H_2O$ | 80.4 | 26.4 | 0.02 | 11 |
| 11 | i-butyric acid | 0.5 $NH_4VO_3$ + 0.5 $Mn(NO_3)_2 \cdot 4 H_2O$ | 80.0 | 26.4 | 0.02 | 10 |
| For comparison: | | | | | | |
| 12 | acetic acid | without catalyst | 42.2 | 25.0 | not determined | >100 |
| 13 | acetic acid | 1.0 $Cu(NO_3)_2 \cdot 3 H_2O$ | 44.1 | 26.1 | not determined | >100 |
| 14 | propionic acid | 1.0 $Mn(NO_3)_2 \cdot 4 H_2O$ | 45.8 | 25.9 | not determined | >100 |

+theory 26.6%

EXAMPLE 15

100 parts of 5,6-dichloroacenaphthene (85% strength), 600 parts of glacial acetic acid, 30 parts of water and 1 part of ammonium vanadate are brought to 130° C. under 4 bars pressure, in a stirred titanium autoclave fitted with a reflux condenser, and 205 parts of 65% strength nitric acid are added uniformly in the course of 2 hours. The pressure is kept constant by operating the relief valve provided above the reflux condenser. The mixture is subjected to an after-oxidation as described in Examples 1 to 11, except that it is conducted for 2 hours at 130° C. under 4 bars, and is then let down, cooled to room temperature and worked up as described in Examples 1 to 11. 72.4 parts of 4,5-dichloronaphthalic acid anhydride containing 26.4% of chlorine and <0.05% of nitrogen and having an iodine color number of 31 are obtained.

EXAMPLE 18

100 parts of 3,5,6-trichloroacenaphthene of 87% purity are oxidized, and purified, as described in Example 2. 73.1 parts of 2,4,5-trichloronaphthalic acid anhydride containing 35.0% of chlorine (theory 35.3%) and having an iodine color number of 11 are obtained.

We claim:
1. In a process for the manufacture of pure halonaphthalic acid anhydrides from haloacenaphthenes by oxidizing the haloacenaphthenes with nitric acid in the presence of vanadate, with out without further metal salts, at an elevated temperature, the improvement which comprises: carrying out the oxidation in a mixture of aliphatic carboxylic acid, water and nitric acid; isolating the reaction product and subjecting the reaction product to an oxidative after-treatment with hypochlorite in aqueous solution at a pH of from 9 to 12 at an elevated temperature.

2. The process of claim 1, wherein 5-chloro-,5,6-dichloro- or 3,5,6-trichloro-acenaphthene is used as the haloacenaphthene.

3. The process of claim 1, wherein nitric acid of about 65% strength is used for the oxidation, and the nitric acid content of the oxidation system is kept at from 0.01 to 30% by weight, preferably from 0.1 to 20% by weight.

4. The process of claim 1, wherein the oxidation is carried out with nitric acid from 70° to 160° C., preferably from 90° to 110° C.

5. The process of claim 1, wherein acetic acid or propionic acid, mixed with up to 15% water, is used as the reaction medium.

* * * * *